(12) United States Patent  (10) Patent No.: US 8,916,730 B2
Dubois  (45) Date of Patent: Dec. 23, 2014

(54) METHOD FOR THE SYNTHESIS OF DIALKOXY ALKANES BY MEANS OF THE SELECTIVE OXIDATION OF ALCOHOLS

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 604 days.

(21) Appl. No.: 12/995,218

(22) PCT Filed: May 28, 2009

(86) PCT No.: PCT/FR2009/051007
§ 371 (c)(1),
(2), (4) Date: Nov. 30, 2010

(87) PCT Pub. No.: WO2009/156655
PCT Pub. Date: Dec. 30, 2009

(65) Prior Publication Data
US 2011/0071322 A1  Mar. 24, 2011

(30) Foreign Application Priority Data
Jun. 3, 2008 (FR) .................................. 08 53667

(51) Int. Cl.
*C07C 41/50* (2006.01)
*C07C 45/38* (2006.01)
(52) U.S. Cl.
CPC ............... *C07C 41/50* (2013.01); *C07C 45/38* (2013.01)
USPC ...................................................... 568/594
(58) Field of Classification Search
CPC ...................................................... C07C 41/50
USPC ...................................................... 568/594
See application file for complete search history.

(56) References Cited

U.S. PATENT DOCUMENTS

| | | | | |
|---|---|---|---|---|
| 3,285,970 A * | 11/1966 | Schaeffer | ...................... | 568/594 |
| 3,346,623 A * | 10/1967 | Young | ...................... | 554/132 |
| 3,471,532 A * | 10/1969 | Young | ...................... | 554/135 |
| 4,250,121 A * | 2/1981 | Mimoun | ...................... | 568/431 |
| 6,166,266 A * | 12/2000 | Hagen et al. | ................. | 568/613 |
| 6,518,463 B2 * | 2/2003 | Wachs et al. | ................. | 568/472 |
| 7,759,525 B2 | 7/2010 | Dubois et al. | | |
| 2005/0059839 A1 | 3/2005 | Liu et al. | | |

FOREIGN PATENT DOCUMENTS

WO  WO 2007/034264 A1 * 3/2007 .............. C07C 41/50
WO  WO 2007/128941    11/2007

OTHER PUBLICATIONS

Pernicone, N., et al., "On the Mechanismof CH3OH Oxidtion to CH2O over MoO3—Fe2 (MoO4) 3 CAtalyst", Journal of Catalyst 14, (1969), pp. 293-302.
Auroux, A., et al, "Microcalorimetric Study of the Acidity and Basicity of Metal Oxide Surfaces", The Journal of Physical Chemistry, vol. 94, (1990), pp. 6371-6379.
Pearson, R., "Physical and Inorganic Chemistry", Journal of the American Chemical Society, (T963), pp. 3533-3539.
Pearson, R. "Hard and Soft Acids and Bases, HSAB, Part 1", Journal of Chemical Education, vol. 45, (1968), pp. 581-587.
Parr, R., et al., "Absolute Hardness : Companion Parameter to Absolute Electronegativity", J. Am Chem. Soc.,, (1983) pp. 7512-7516.
Sambeth, J. et al., "Study of the Adsorption/ Oxidation of Methanol over Vanadium Pentoxide", Adsorption Science Technology, (1995), pp. 171-180.
Fournier, M., et al., "Evidence of B—MoO3 Formation during Thermal Treatment of Silica-supported 12-Molybdophosphoric Acid Catalysts", J. Chem. Soc., Chem. Commun., (1994), pp. 307-308.
Tatibouet, J-M, et al., "Catalytic Oxidation of Methanol by 12-Molybdosilicic Acid Supported on Silica: Dispersion Effect", J. chem. Soc., Chem. Commun., (1988), pp. 1260-1261.
Tossell, J., "Boric acid, "carbonic" acid, and N-containing oxyacids in aqueous solution: Ab initio studies of structure, pka, NMR shifts, and isotopic fractionations", Elsevier, (2005), pp. 5647-5658.
Burczyk, B. "Sulfur Dioxide as a Catalyst in Acetal Synthesis from Allphatic Aldehydes or Ketones and Alcohols", Institute of Organic and PolymerTechnology, (1980), pp. 173-176.
Le Page, J-F, et al., "Catalyse de contact", Institut Francais du Petrole, Editions Technip (1978), pp. 385-393.
Twigg, M., "Catalyst Handbook", Wolfe Publishing Ltd, (1989), pp. 490-503.
Pernicone, N., et al., "On the Mechanismof CH3OH Oxidtion to CH2O over MoO3-Fe2 (MoO4) 3 CAtalyst", Journal of Catalyst 14, (1969), pp. 293-302.
Liu, H. et al., "Selective Oxidation of Methanol and Ethanol on Supported Ruthenium Oxide Clusters at Low Temperatures", American Chemical Society, (2005), pp. 2155-2163.
Auroux, A., et al., "Microcalorimetric Study of the Acidity and Basicity of Metal Oxide Surfaces", The Journal of Physical Chemistry, vol. 94, (1990), pp. 6371-6379.
Damjanovic, L. et al., "Heterogeneous Catalysis of Solids", Elsevier B.V., (2008), pp. 387-485.
Pearson, R., "Physical and Inorganic Chemistry", Journal of the American Chemical Society, (1963), pp. 3533-3539.
Pearson, R., "Acids and Bases", Science vol. 151, (1966), pp. 172-177.
Pearson, R., "Hard and Soft Acids and Bases", Chemistry in Britain, (1967), pp. 103-107.
Pearson, R., "Hard and Soft Acids and Bases, HSAB, Part 1", Journal of Chemical Education, vol. 45, (1968), pp. 581-587.
Pearson, R. "Hard and Soft Acids and Bases, HSAB, Part II", Journal of Chemical Education, vol. 45, (1968), pp. 643-648.

(Continued)

*Primary Examiner* — Rosalynd Keys
(74) *Attorney, Agent, or Firm* — Smith, Gambrell & Russell, LLP

(57) ABSTRACT

The invention relates to a method for the synthesis of dialkoxyalkanes by means of the partial selective oxidation of a light alcohol. According to said method, the light alcohol is oxidized in the presence of molecular oxygen or a gas containing molecular oxygen, and a solid oxidation catalyst based on at least one metal in a reactive medium comprising a gaseous phase containing an acid compound according to the Pearson classification, having a pKa of less than 6.3 in solution in water. The reaction is carried out in a vapor or in a liquid phase.

7 Claims, No Drawings

(56) References Cited

OTHER PUBLICATIONS

Parr, R., et al., "Absolute Hardness: Companion Parameter to Absolute Electronegativity", J. Am Chem. Soc,., (1983) pp. 7512-7516.

Marcilly, C., "Catalyse acido-basique", Editions Technip, (2003), p. 71.

Sambeth, J. et al., "Study of the Adsorption/Oxidation of Methanol over Vanadium Pentoxide", Adsorption Science Technology, (1995), pp. 171-180.

Fournier, M., et al., "Evidence of B-MoO3 Formation during Thermal Treatment of Silica-supported 12- Molybdophosphoric Acid Catalysts", J. Chem. Soc., Chem. Commun., (1994), pp. 307-308.

Tatibouet, J-M, et al., "Catalytic Oxidation of Methanol by 12-Molybdosilicic Acid Supported on Silica: Dispersion Effect", J. chem. Soc., Chem. Commun., (1988), pp. 1260-1261.

Twigg, M., "Catalyst Handbook, Second Edition", Wolfe Publishing Ltd, (1989), pp. 498-499.

Le Page, J-F, et al., "Catalyse de Contact", Editions Technip, (1978), pp. 400-401.

Zabetakis, M., "Flammability Characteristics of Combustible Gases and Vapors", Bureau of Mines, (1965), pp. 66-68.

Techinal Report isa-tr12.13.01, "Flammability Characteristics of Combustible Gases and Vapors", (1999), fig. 75 and 76 and table 13.

* cited by examiner

METHOD FOR THE SYNTHESIS OF DIALKOXY ALKANES BY MEANS OF THE SELECTIVE OXIDATION OF ALCOHOLS

One subject of the present invention is a method for the synthesis of dialkoxy alkanes by selective oxidation of light alcohols.

The dialkoxyalkanes from the method of the invention correspond to the following general formula: RR'CH—O—CRR'—O—CHRR' in which R and R' are either H, or a $CH_3$—$(CH_2)_n$— radical, n being between 0 and 2, such that the total number of carbon atoms of the R and R' radicals is ≤3.

These compounds are obtained by oxidation of light alcohols, that is to say linear alcohols comprising from 1 to 4 carbon atoms. These are primary alcohols such as methanol, ethanol, 1-propanol and 1-butanol or secondary alcohols such as 2-propanol (or isopropanol) or 2-butanol.

When the synthesis reaction is carried out with primary alcohols, the general formula of the dialkoxyalkanes is simplified: $RCH_2$—O—CHR—O—$CH_2R$. This is the formula of the most industrially sought-after dialkoxyalkanes, namely dimethoxymethane (or methylal) and 1,1-diethoxyethane (or acetal).

The methods for oxidation of alcohols and especially light monoalcohols have been well known for at least one century. Reference may be made, on this subject, to works such as that of the Institut Francais du Pétrole [French Institute of Oil], "Catalyse de Contact" [Contact Catalysis] published by Editions Technip (1978) pages 385-393 or the Catalyst Handbook by M. V. Twigg published by Wolfe Publishing Ltd (1989) pages 490 to 503. They are generally used to form aldehydes (formol from methanol) or acids or esters.

It is furthermore known that the oxidation of methanol in the presence of various catalysts results, at low temperature, in the production of a not very selective mixture of various oxidized compounds such as, in particular, formaldehyde, methyl formate or methylal (dimethoxymethane).

The concomitance of these various reactions is illustrated, for example, by the articles by N. Pernicone at al. in "On the Mechanism of $CH_3OH$ Oxidation to $CH_2O$ over $MoO_3$—$Fe_2(MoO_4)_3$ Catalyst" published in Journal of Catalysis 14, 293-302 (3969) and by Haichao Liu and Enrique Iglesia published in J. Phys. Chem. B (2005), 109, 2155-2163 "Selective Oxidation of Methanol and Ethanol on Supported Ruthenium Oxide Clusters at Low Temperatures".

The various catalytic reactions then brought into play with methanol may be illustrated by the following scheme:

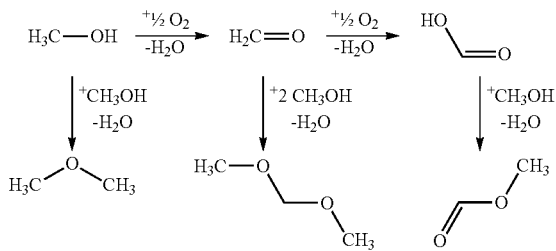

The same scheme may be transposed to ethanol and to other light alcohols.

The conventional methods for oxidation of alcohols target the production of the aldehyde by a simple oxidation of the alcohol and correspond to the following mechanism, in the case of primary alcohols:

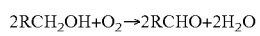

$2RCH_2OH+O_2 \rightarrow 2RCHO+2H_2O$

This oxidation is carried out in the gas phase in the presence of a silver catalyst at a temperature of around 600 to 700° C., or molybdenum-iron mixed oxide type catalysts at a temperature between 200 and 300° C. In the latter case, the oxygen present within the reaction medium is in excess with respect to the stoichiometry of the reaction, but used in dilute form, the substantially equal partial pressures of $O_2$ and alcohol are around a few %, therefore having an $O_2$/alcohol molar ratio >1.

The aforementioned article by N. Pernicone et al. refers to a method for the industrial synthesis of formaldehyde, the Montedison process, catalyzed by a mixed oxide based on molybdenum and iron and cites a study on the reaction mechanism of this type of reaction, including parasitic secondary reactions.

The methods for complete oxidation of the light alcohols make it possible to synthesize acids (then the corresponding esters) according to the following overall reaction:

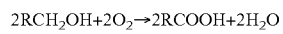

$2RCH_2OH+2O_2 \rightarrow 2RCOOH+2H_2O$ which is the result of the following two steps:

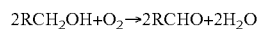

$2RCH_2OH+O_2 \rightarrow 2RCHO+2H_2O$

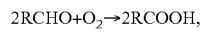

$2RCHO+O_2 \rightarrow 2RCOOH,$ which is followed, where appropriate, by the esterification:

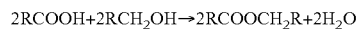

$2RCOOH+2RCH_2OH \rightarrow 2RCOOCH_2R+2H_2O$

To illustrate the complete oxidation resulting in formic acid or its ester, methyl formate, mention may be made of Patent Application US 2005/0059839 A1, which describes catalysts for the oxidation of methanol composed of platinum-group metals (ruthenium) deposited on a support. This Application corresponds to the studies by H. Liu and E. Iglesia targeted in the abovementioned publication.

The use of an excess of oxygen at a relatively high temperature may result in complete oxidation and therefore in the acid via successive oxidations of the alcohol and of the aldehyde formed and may even, if precautions are not taken, go further still to result in the "combustion" of the acid, producing carbon dioxide and water.

The methods of "partial" oxidation of monoalcohols are also known. It is known, for example, to directly oxidize methanol $CH_3OH$ to dimethoxymethane and also ethanol to diethoxyethane.

This oxidation reaction is carried out in two steps according to the following reaction processes:

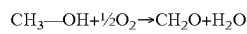

$CH_3$—OH+½$O_2 \rightarrow CH_2O+H_2O$

$CH_2O+2CH_3$—OH$\rightarrow CH_2(OCH_2)_2+2H_2O$

The process is analogous for ethanol:

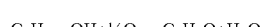

$C_2H_5$—OH+½$O_2 \rightarrow C_2H_5O+H_2O$

$C_2H_5O+2C_2H_5$—OH$\rightarrow CH_2(OC_2H_5)_2+2H_2O$

As can be seen, this method results in the formation, as an intermediate product, of the aldehyde that corresponds to the initial alcohol. In the method, the catalytic reactions involved target, from an industrial point of view, the synthesis of acetals, the other oxidation products having their specific synthesis pathways.

However, experience shows that the oxidation of monoalcohols to acetals with its two steps, oxidation and acetalization, unfortunately results in numerous by-products such as aldehydes, formol or acetaldehyde depending on the initial alcohol, diemethyl ether, ether (diethyl ether), ethylene or aldols as a function of the secondary reactions due to the synthesis conditions.

Unlike the methods for synthesizing aldehydes, acids or esters, the methods of partial oxidation of light alcohols make it possible to synthesize dialkoxyalkanes according to the following overall reaction that corresponds to primary alcohols:

$$6RCH_2OH+O_2 \rightarrow 2RCH_2ORCHOCH_2R+4H_2O$$

which is the result of two successive steps:

$$2RCH_2OH+O_2 \rightarrow 2RCHO+2H_2O$$

$$2RCHO+4RCH_2OH \rightarrow 2RCH_2ORCHOCH_2R+2H_2O$$

Similar mechanisms are used in the oxidation reactions of secondary light alcohols such as 2-propanol and 2-butanol.

The initial oxidation of the secondary alcohol leads to a ketone of formula $CH_3$—$CO$—$CH_3$ with isopropanol and $CH_3$—$CO$—$C_2H_5$ with 2-butanol. The following reaction step of the ketone with the light alcohol leads to dialkoxyalkanes of respective formulae $(CH_3)_2CH$—$O$—$C(CH_3)_2$—$O$—$CH(CH_3)_2$ and $(C_2H_5)(CH_3)CH$—$O$—$C(CH_3)(C_2H_5)$—$O$—$CH(CH_3)(C_2H_5)$.

The overall reaction for the oxidation to the dialkoxyalkane 2,2-diisopropoxypropane from isopropanol is summarized as follows.

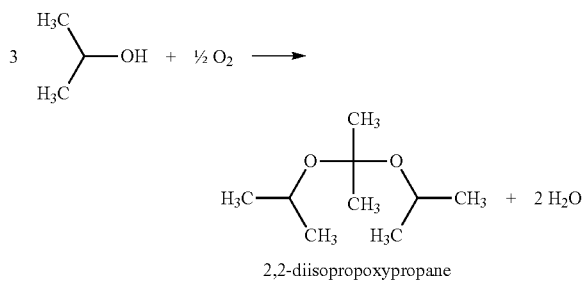

2,2-diisopropoxypropane

In order to be thorough on the prior art as regards the oxidation of alcohols, it should be noted that the synthesis of oxidized compounds of methanol, such as formaldehyde, may be carried out by using "related" reactions, i.e. reactions that have a similar objective, to synthesize compounds of a higher level of oxidation, but based on reaction mechanisms that are substantially different, namely non-oxidizing dehydrogenation or oxidizing dehydrogenation (oxydehydrogenation) carried out with a deficit of oxygen according to the following reaction mechanism:

$$RCH_2OH \rightarrow RCHO+H_2,$$

with production of hydrogen and also of water in the case of oxydehydrogenation. This reaction is carried out in the gas phase in the presence, for example, of a reduced copper catalyst or a metallic silver catalyst at temperatures generally between 600 and 700° C. On this subject, the "Catalyst Handbook" cited previously may be consulted.

Research studies having an industrial objective have therefore turned towards the study of the operating conditions, temperature, liquid phase or gas phase and especially catalysts for the method that make it possible to obtain the dialkoxyalkane. The problem to be solved is to obtain, by direct oxidation of the alcohol feedstock, the desired "target" product with, simultaneously, a high conversion and a high selectivity.

It has been observed in the great majority of these reactions for the partial oxidation of light alcohols that the main reactions are accompanied by secondary reactions that result in undesirable by-products, the separation of which from the reaction medium is sometimes difficult.

As examples, mention may be made, during the partial oxidation of monoalcohols, of the formation of products such as aldehydes, formol, acetaldehyde or ketones having three or four carbon atoms, depending on the initial alcohol (the reaction is then "blocked" in its first step), dimethyl ether, ether (diethyl ether), ethylene or aldols.

DETAILED DESCRIPTION OF THE INVENTION

It has been discovered by the applicant that the parasitic reactions may be caused by the nature of the catalysts used for the oxidation. The Applicant Company has surprisingly discovered that the catalysts described for the catalysis of the reaction for the partial oxidation of light alcohols which are solid multiphase or homogeneous materials that are insoluble in the reaction medium may have certain undesirable sites of "basic" nature which are probably the cause of the formation of by-products by reaction mechanisms that are sometimes not very predictable.

The objective of the present invention is to overcome these drawbacks by implementing the method while adding, within the gaseous reaction medium, a compound capable of attaching at least temporarily to these sites and, by inhibiting them during the process, of preventing for the most part the formation of by-products.

The present invention targets the synthesis of dialkoxy alkanes corresponding to the following general formula: RR'CH—O—CRR'—O—CHRR' in which R and R' are either H, or a $CH_3$—$(CH_2)_n$— radical, n being between 0 and 2 and such that the total number of carbon atoms of the R and R' radicals is ≤3 by partial selective oxidation of a light alcohol comprising from 1 to 4 carbon atoms, characterized in that it is carried out in the presence of oxygen and of a solid oxidation catalyst in a reaction medium comprising a gas phase containing an acid compound.

The expression "acid compound" is understood, within the meaning of the present invention, to mean a compound which, besides that which will be specified below, will exhibit, in solution in water, a pKa of less than 6.3. In particular, $CO_2$ is not an acid within the meaning of the present invention.

The light alcohols used are either primary alcohols such as methanol, ethanol, 1-propanol, isopropanol, n-butanol and 1-butanol, or secondary alcohols such as 2-propanol (or isopropanol) or 2-butanol.

The oxidation is carried out by contact in the gas phase by means of oxygen or a gas that contains molecular oxygen (for example air).

The oxidation is carried out in the presence of a solid catalyst based on at least one metal chosen from Mo, V, W, Re, Cr, Mn, Fe, Co, Ni, Cu, Zn, Sn, Te, Sb, Bi, Pt, Pd, Ru, Rh. These metals are present in metallic form or in the oxide, nitrate, carbonate, sulfate or phosphate form.

These catalysts all have a certain acidity which can be measured according to the Hammett method. This $H_0$ acidity is in general less than +2, in the reference scale with Hammett indicators. The table given on page 71 of the publication on acid-base catalysis (C. Marcilly), Vol. 1 in Editions Technip (ISBN No. 2-7108-0841-2) illustrates examples of solid catalysts in this acidity range.

The catalysts selected for this reaction are acid solids. The acidity of the solids may be measured in numerous ways and the Hammett method is only one of these ways.

It has been observed by the Applicant that these naturally acidic catalysts may also comprise sites that are instead of basic nature. On this subject, mention will be made of the publications by Aline Auroux where various methods for measuring acidity scales of solids are described such as: A. Auroux and A. Gervasini, "J. Microcalorimetric Study of the Acidity and Basicity of Metal Oxide Surfaces" Phys. Chem., (1990) 94, 6371-79 and L. Damjanovic and A. Auroux, in "Handbook of Thermal Analysis and calorimetry", Vol. 5, Chapter 11 pages 387-485; Recent Advances, Techniques and Applications, M. E. Brown and P. K. Gallager, editors (2008 Elsevier B. V.).

These studies illustrate, in particular, that a solid is rarely constituted either of uniquely acidic sites or of uniquely basic sites. Acidic solids have, most of the time, both acidic sites, in the majority, but also some basic sites. This dichotomy is particularly illustrated in the article by A. Auroux and A. Gervasini on page 6377 where Figure 13 shows that one and the same oxide may simultaneously adsorb an acid compound such as $CO_2$ and a basic compound such as $NH_3$. Without wishing to be tied to any one theory, it is believed that the latter contribute to the formation of by-products in the method.

The method is carried out in the presence, in the gas phase of the reaction medium, of an added acid compound which has an affinity with the undesirable basic sites borne by the catalyst.

This compound will be chosen from the hard and soft acids as they are defined in the Pearson classification illustrated in the following articles: R. G. Pearson, J. Am. Chem. Soc., 85, 3533 (1963); R. G. Pearson, Science, 151 (1966) 172; R. G. Pearson, Chemistry in Britain, March 1967, 103; R. G. Pearson, J. Chemical Education, Vol. 45 No. 9 (1968) 581 and Vol. 45 No. 10 (1968) 643; R. G. Parr and R. G. Pearson, J. Am. Chem. Soc, (1983) 105, 7512, and also in the work by C. Marcilly, referenced above, on pages 34 onwards using the scale based on the Pearson theory and that are capable, if they are not already gaseous, of passing, under the operating conditions, into the gas phase of the reaction medium.

This acid compound will be chosen especially from $SO_3$, $SO_2$, $NO_2$, etc. It would not be outside the scope of the invention if a mixture of these compounds were used, indeed it is possible to use a mixture of compounds combining various acidities in order to inhibit the various basic sites present on the catalyst. Indeed, according to Pearson's theory, it appears that hard acids prefer to associate with hard bases and soft acids with soft bases.

The content of acid compounds will depend on the nature of the catalyst chosen for the reaction. It will generally be between 1 and 3000 ppm of the gas phase.

The catalysts used in the method of the invention are catalysts that are already known for the oxidation of alcohols and also for the partial oxidation of said alcohols to dialkoxyalkanes. They have already been the subject of various publications.

Mention may be made of the use of a rhenium-antimony-based catalyst ($SbRe_2O_6$) for manufacturing methylal by oxidation of methanol described in U.S. Pat. No. 6,403,841.

Furthermore, J. Sambeth, L. Gambaro and H. Thomas, *Adsorption Science Technology* (1995) page 171, recommend the use of vanadium pentoxide for the oxidation of methanol, methylal being one of the products resulting from the reaction.

The studies of several teams have focused on the use of molybdenum-based catalysts which come under a preferred embodiment variant of the method of the invention.

Mention may be made of the catalyst that consists of a heteropolyacid of formula $H_{3+n}XV_nMo_{12-n}O_{40}$, where X represents phosphorus or silicon, and n a value from 0 to 4 and in particular a $H_5PV_2Mo_{10}O_{40}$ catalyst over silica, described in US patent application No. 2005/0154226 A1 dedicated to a method of producing methylal by oxidation of methanol and/or dimethyl ether.

Mention may also be made of the catalysts of formula $H_3PMo_{12}O_{40}$/silica and $H_4SiMo_{12}O_{40}$/silica described by M. Fournier, C. Rocchicciolo-Deltcheff, et al., for the oxidation of methanol (*J. Chem. Soc., Chem. Commun.* 1994, 307-308) and (*J. Chem. Soc., Chem. Commun.* 1998, 1260-1261).

The Applicant has also filed a patent application, WO 2007/034264, describing the use, in this type of method for partial oxidation of methanol, of a catalyst consisting of a mixed oxide based on molybdenum and vanadium combined, where appropriate, with other metallic elements. The preferred catalyst corresponded to the formula $Mo_{12}V_3W_{1.2}Cu_{1.2}Sb_{0.5}O_x$, x being a numerical value determined by the degree of oxidation of the other elements.

In most cases, these catalysts consist of metal oxides, generally of mixed oxides of metals.

The family of catalysts based on molybdenum of oxide type corresponds to the following general formula:

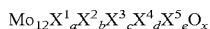

in which Mo=molybdenum; O=oxygen; $X^1$=at least one element chosen from iron, nickel, cobalt, manganese, tin and copper; $X^2$=at least one element chosen from bismuth, antimony, tellurium, indium, aluminum and chromium, $X^3$=at least one element chosen from phosphorus, tungsten, titanium, vanadium, tantalum and niobium; $X^4$=at least one element chosen from alkaline-earth metals, lanthanum or cerium; $X^5$ is at least one element chosen from alkali metals; and a, b, c, d and e are indices, the values of which are $0 \leq a \leq 20$; $0 \leq b \leq 4$; $0 \leq c \leq 5$; $0 \leq d \leq 2$; $0 \leq e \leq 2$ such that a+b>0; and x is a numerical value determined by the degree of oxidation of the other elements.

In the method of the invention, use will preferably be made of mixed oxides of molybdenum and tungsten, of molybdenum and vanadium, of molybdenum and cerium, of molybdenum and bismuth (bismuth molybdate), of molybdenum and manganese or mixed oxides of molybdenum and iron. The catalysts preferred in the method of the invention are those based on molybdenum and iron. Mention may be made, for example, of the mixed oxides of formulae: $Mo_{12}BiFe_{3.7}CO_{4.7}Ni_{2.6}K_{0.09}Sb_1Si_{7.9}O_x$, $Mo_{12}BiFe_{3.7}CO_{4.7}Ni_{2.6}K_{0.09}Ti_{0.5}S_{i19}O_x$ or $MoO_3$—$Fe_2(MoO_4)_3$.

The reaction will generally be carried out at a temperature between 10 and 400° C. and under a pressure between 50 and 1000 kPa and at a flow rate for introducing the feedstock mixture such that the hourly volume velocity (HVV), that is to say the flow rate of reaction mixture relative to the volume of catalyst used, will especially be between 2000 and 100 000 $h^{-1}$.

Preferably, the oxidation is carried out by contact, in the vapor phase, at a temperature in particular between 100 and 350° C., and more preferably between 200 and 300° C. The pressure will preferably be between 100 and 500 kPa. The space velocity for introducing the reaction mixture will preferably be between 11 000 and 44 000 $h^{-1}$.

The reaction according to the invention may also be carried out in the liquid phase.

When the reaction is carried out in the liquid phase in the presence of a catalyst, at a temperature ranging from 150° C. to 500° C., preferably between 250° C. and 350° C., and at a pressure greater than 5 bar and preferably between 20 and 80 bar.

When the reaction is carried out in the gas phase, various process technologies can be used, namely a fixed-bed process, a fluidized-bed process or a circulating fluidized-bed process. In the first two processes, fixed-bed or fluidized-bed, the regeneration of the catalyst may be separate from the reaction.

It may be carried out ex situ, for example by extraction of the catalyst and combustion in air or with a gas mixture containing molecular oxygen. In this case, the temperature and the pressure at which the regeneration is carried out do not need to be the same as those at which the reaction is carried out. Preferably, the addition of the acid compound, which is acid within the meaning of Pearson, is not carried out during the regeneration.

According to the method of the invention, the regeneration may be carried out continuously in situ, at the same time as the reaction considering the presence of a small amount of molecular oxygen or of a gas containing molecular oxygen in the reactor. In this case, the regeneration is similar to an inhibition of the deactivation and takes place at the temperature and at the pressure of the reaction. Due to these particular conditions where the regeneration takes place continuously, the injection of the gaseous acid compound is simultaneous.

In the circulating fluidized-bed process, the catalyst circulates in two vessels, a reactor and a regenerator. The injection of the gaseous acid compound is preferably carried out at the reactor.

Furthermore, it is well known that all the methods for the oxidation of alcohols, and therefore of fuels, may be carried out depending on the choices of compositions of the ternary mixture under inflammability conditions of the alcohol-oxygen mixture. These conditions are not an obstacle that nullifies an industrial exploitation but they require operating precautions which, due to their cost, should be avoided as much as possible. It is therefore preferable to operate under strict safety conditions, that is to say by making sure not to work in the flammability range of the alcohol-oxygen mixture.

In order to do this, reference may be made to certain determinations of this range in various cases taking into account the components of the mixture, the operating temperature and the pressure. The diagram from Figure 1 illustrates this flammability range for a ternary methanol-oxygen-inert gas mixture at a temperature of 25° C. and at atmospheric pressure.

In order to determine the optimum reaction conditions outside of the flammability range, reference may be made to various publications on the subject. Apart from the "Catalyst Handbook" page 498 and the work "Catalyse de Contact" [Contact Catalysis], page 400 that have already been mentioned, mention may also be made of the article by Michael G. Zabetakis "Flammability Characteristics of Combustible Gases and Vapors", Bureau of Mines Bulletin 627, pages 66 to 68 and the Technical report ISA-TR12.13.01-1999 "Flammability Characteristics of Combustible Gases and Vapors" FIGS. 75 and 76 and table 13.

The appended Figure 1 is presented to better illustrate the operability conditions, outside of the flammability ranges, of the method that is the subject of the present invention under standard temperature and pressure conditions, 25° C. and 1 atm.

In Figure 1, the bold lines 1 and 2 specify the concentrations that are respectively the lower (1) and upper (2) flammability limits. They define, with the methanol-$O_2$ axis, the flammability range of the mixture which substantially takes the shape of a triangle (Zone 0), the apex of which is the maximum oxygen concentration (MOC). The points denoted by LFL (Air) and UFL (Air) correspond to these lower and upper limits in the case of using air as an oxidant. Between these lines (1) and (2) the mixture is in the flammable Zone 0. The portions located above these lines illustrate non-flammable mixtures. The right-hand portion, Zone 3, is that where the concentration of alcohol is low and that of oxygen is larger or smaller but always below the flammability threshold, whereas, in the left-hand portion, Zones 1 and 2 correspond to a low oxygen content (above the flammability threshold). Lines 3, 4 and 5 correspond to the stoichiometries of the main oxidation reactions of the alcohol, in this case methanol; a transposition to ethanol could be easily carried out using the appropriate flammability diagram. Line 3 corresponds to the combustion of methanol ($CH_3OH + 3/2 O_2 \rightarrow CO_2 + 2H_2O$), line 4 to the oxidation to formol ($CH_3OH + \frac{1}{2}O_2 \rightarrow CH_2O + H_2O$), line 5 to the synthesis of methylal ($3CH_3OH + \frac{1}{2}O_2 \rightarrow CH_3OCH_2OCH_3 + H_2O$) and finally line 6 to air, that is to say the straight line joining the methanol apex to the 80/20 $N_2$ (inert)/$O_2$ mixture.

Zone 1 corresponds to mixtures in which an oxygen content below that of air is used (use of diluted air). It is located entirely above line 6.

Zone 2 corresponds to mixtures in which an oxygen content greater than that of air is used. It is located entirely below line 6.

Inside these two zones it is possible to provide some information specific to the methylal formation reaction (line 5). Specifically, if the straight line parallel to the left-hand axis is plotted passing through the apex of the flammable zone (Zone 0): line 7, zone 1 is delimited into two portions 1d and 1g on the one hand and 1' on the other hand. In the Zone 1d/1g, the oxygen content is still below the MOC and there is the guarantee of therefore being outside of the flammability range. In zone 1', there is more oxygen than the MOC, but while still being outside of the flammability range. On either side of line 5 there are Zones 1g and 1d. In Zone 1g, there is less oxygen than the stoichiometry, which mathematically will not make it possible to have 100% yield of methylal. In zone 1d, there is more oxygen than the stoichiometry for the synthesis of methylal; it is therefore possible to hope for high conversions and yields. It is possible in each of Zones 1 and 2 to distinguish zones: 1d, 1g and 1' and 2d, 2g and 2'.

In Zones 1, the reaction may be carried out with air as an oxidant.

In Zones 2d, 2g and 2', the reaction should be carried out with an addition of molecular oxygen. Zone 3 is the zone delimited by the lower flammability limit.

Zones 1d, 1g and 2g are delimited by the maximum oxygen concentration (MOC). Below this oxygen content, there is the guarantee of being outside of the flammability limits. It is therefore preferred to work in this zone for safety reasons.

Zones 1', 1d and 1g and 2g, 2d and 2' are delimited by the line of stoichiometry for the methanol→methylal reaction ($6CH_3OH/O_2$). To the right of this line, there is enough oxygen to have a complete conversion of methanol at 100% selectivity to methylal; on the left, there is not enough oxygen and the conversion will only be partial. It is therefore preferred to work in zones 1', 1d and 2'.

In the method of the invention, the preferred zones are Zones 1d, 1' and 1g in which it is possible to work with high contents both of alcohols (30 to 40% or even or 60% by volume) and of oxygen, of around 15%, while still working with air as a source of oxygen and being free from using a large source of inert gas. It should be noted that the maximum content of $O_2$ depends on the alcohol and it rises.

It is preferred to use an oxidant gas that is rich in air in order to reduce electricity consumption at the gas compressors. In this configuration, it is not necessary to recycle oxygen-depleted gases of the reaction in order to dilute the oxygen of the air of reaction and therefore the method is simplified.

This ternary diagram may be transposed, on the one hand, with the same constituents to different temperature and pressure conditions and, on the other hand, to other alcohols, referring to the publications and especially that of Zebetakis, which also illustrates the ethanol diagram. Represented on page 67 of this publication is a table from which it is possible to deduce the maximum oxygen concentrations according to the alcohol used.

Another subject of the invention is therefore the use of the method as defined above for the synthesis of diethoxyethane by oxidation of ethanol.

The following examples further illustrate the present invention without however limiting the scope thereof.

Example 1

Reaction Conditions

The evaluation of the catalyst was carried out in a fixed-bed reactor. The flow of helium and of oxygen was controlled by mass flow meters. The gas stream passed into an evaporator/saturator containing methanol. The evaporator was either at ambient temperature or heated by heating tapes. The temperature of the saturator was adjusted in order to control the partial pressure of methanol. The temperature of the gas mixture was controlled by a thermocouple at the top of the saturator.

The gas mixture was then sent to the reactor which was placed in an oven. The reaction temperature was measured using a thermocouple which was in the catalytic bed.

The gaseous effluents were analysed by in-line gas chromatography using a microGC equipped with 2 columns (molecular sieve and Plot U).

The catalyst was milled and the 250 micron particle size fraction was mixed with a double amount of silicon carbide of the same particle size and placed in the glass reactors.

Calibration of the MicroGC was carried out with reference gas mixtures, and calibration for the condensable products (dimethoxymethane, methanol, methyl formate) was carried out using the evaporator/saturator.

Example 2

Oxidation Reaction of Methanol

The catalyst was prepared as in example 1 of patent application WO 2007/034264. The catalyst corresponded to the formula $Mo_{12}V_3W_{1.2}Cu_{1.2}Sb_{0.5}O_x$, x being a numerical value determined by the degree of oxidation of the other elements.

150 mg of this catalyst were mixed with 300 mg of silicon carbide and charged into the reactor.

The catalyst was activated under a gas stream composed of a mixture of helium and oxygen (48 Nml·min$^{-1}$/12 Nml·min$^{-1}$) at 340° C. for 15 hours and 30 minutes. Next, the temperature of the catalyst was dropped to 280° C. and the data were recorded. After stabilization of the temperature, the efficiency of the catalyst was recorded. After acquisition of the data, the temperature of the catalyst was reduced to the following temperature: 280° C., 270° C., 260° C. and 250° C., where the data were recorded.

The flow rates of oxygen and helium were respectively 4.7 and 46.3 Nml·min$^{-1}$ and the concentration of methanol was set to 7.5%.

The results are presented in table 1 below.

TABLE 1

| Catalyst | Temperature (° C.) | Conversion (%) | Selectivities (%) | | | | | | |
|---|---|---|---|---|---|---|---|---|---|
| | | | DMM | F | DME | MF | CO | $CO_2$ | Total |
| MoVWSbCu | 249 | 26.3 | 88.2 | 2.5 | 6.8 | 2.0 | 0.4 | 0.0 | 100 |
| | 260 | 32.8 | 89.9 | 1.7 | 5.9 | 1.9 | 0.6 | 0.0 | 100 |
| | 269 | 43.2 | 90.0 | 2.2 | 5.4 | 1.5 | 0.9 | 0.0 | 100 |
| | 280 | 57.0 | 89.2 | 3.3 | 5.1 | 1.2 | 1.2 | 0.0 | 100 |

Example 3

According to the Invention

The preceding example was reproduced but adding 1000 ppm (vol) of $SO_2$ to the reaction mixture. The results are presented in table 2 below. The conversion to dimethoxymethane (DMM) is higher.

TABLE 2

| Catalyst | Temperature (° C.) | Conversion (%) | Selectivities (%) | | | | | | |
|---|---|---|---|---|---|---|---|---|---|
| | | | DMM | F | DME | MF | CO | $CO_2$ | Total |
| MoVWSbCu | 240 | 12.2 | 91.1 | 2.0 | 5.6 | 1.0 | 0.3 | 0.0 | 100 |
| | 260 | 33.1 | 90.9 | 1.4 | 5.8 | 1.5 | 0.4 | 0.0 | 100 |
| | 280 | 58.6 | 89.9 | 2.9 | 5.1 | 1.0 | 1.1 | 0.0 | 100 |

The following examples further illustrate the present invention without however limiting the scope thereof.

Example 4

Reaction Conditions

The evaluation of the catalysts was carried out in a fixed-bed reactor. The flow of helium and of oxygen was controlled by mass flow meters. The gas stream passed into an evaporator/saturator containing methanol. The evaporator was either at ambient temperature or heated by heating tapes. The temperature of the saturator was adjusted in order to control the partial pressure of methanol. The temperature of the gas mixture was controlled by a thermocouple at the top of the saturator.

The gas mixture was then sent to the reactor which was placed in an oven. The reaction temperature was measured using a thermocouple which was in the catalytic bed.

The gaseous effluents were analysed by in-line gas chromatography using a microGC equipped with 2 columns (molecular sieve and Plot U).

The catalysts were milled and the 250 micron particle size fraction was mixed with a double amount of silicon carbide of the same particle size and placed in the glass reactors.

Calibration of the MicroGC was carried out with reference gas mixtures, and calibration for the condensable products (dimethoxymethane, methanol, methyl formate) was carried out using the evaporator/saturator.

Example 5

Oxidation Reaction of Methanol (According to the Invention)

151 mg of an iron molybdate catalyst MFM3-MS supplied by MAPCO were mixed with 300 mg of silicon carbide and charged into the reactor. MFM3-MS catalyst: outer diameter=3.9 mm, inner diameter=1.85 mm, height=4.04 mm.

The catalyst was first activated under a helium/oxygen stream (48 Nml/min-12 Nml/min) at 340° C. for 15 hours and 30 minutes. Next, the temperature was brought to 250° C. and the acquisition of data was started. After stabilization, the performance of the catalyst was recorded. Next, the temperature of the catalyst was increased in stages and at each level (260, 271 and 281° C.) data were taken.

The flow rates of oxygen and helium were respectively 6.7 and 26.4 Nml/min and the concentration of methanol was adjusted to 37% (conditions: methanol/$O_2$/inert gas: 37/13/50) for an HVV of 22 000 ml·$h^{-1}$·$g^{-1}$. The $SO_2$ concentration was 1000 ppm (vol) relative to the total flow rate.

The conversion and selectivity results obtained during the catalytic oxidation of methanol are given in table 1 (DMM=methylal; F=formol; DME=dimethyl ether; MF=methyl formate; CO=carbon monoxide; $CO_2$=carbon dioxide).

TABLE 3

| Catalyst | Temperature (° C.) | Conversion (%) | Selectivities (%) | | | | | | Total |
|---|---|---|---|---|---|---|---|---|---|
| | | | DMM | F | DME | MF | CO | $CO_2$ | |
| MFM3-MS | 250 | 25.9 | 95.3 | 0.1 | 4.2 | 0.4 | | | 100 |
| "Iron | 260 | 33.2 | 96.3 | 0.2 | 3.2 | 0.3 | | | 100 |
| molybdate" | 270 | 46.0 | 94.7 | 1.0 | 3.8 | 0.5 | 0.0 | | 100 |
| | 280 | 55.1 | 91.8 | 3.2 | 4.5 | 0.4 | 0.1 | | 100 |

Example 6

The preceding example was reproduced but in the absence of $SO_2$.

TABLE 4

| Catalyst | Temperature (° C.) | Conversion (%) | Selectivities (%) | | | | | | Total |
|---|---|---|---|---|---|---|---|---|---|
| | | | DMM | F | DME | MF | CO | $CO_2$ | |
| MFM3-MS | 250 | 25.3 | 94.3 | 0.1 | 4.9 | 0.6 | — | — | 100 |
| "Iron | 260 | 32.3 | 94.3 | 0.3 | 4.9 | 0.6 | — | — | 100 |
| molybdate" | 271 | 46.5 | 92.7 | 1.3 | 5.2 | 0.7 | 0.1 | — | 100 |
| | 281 | 55.7 | 89.8 | 4.2 | 5.3 | 0.6 | 0.1 | — | 100 |

Example 7

Operating Conditions for the Selective Oxidation of Ethanol

The catalyst was tested in a fixed-bed reactor. The flow rates of helium and of oxygen were controlled by a mass flow meter. The gas mixture passed through an evaporator/saturator filled with ethanol. The evaporator was either at ambient temperature or heated by a heater cable. The temperature of the saturator was adjusted and controlled in order to obtain the desired partial pressure of ethanol. The temperature was measured using a thermocouple at the outlet of the saturator.

The reaction mixture fed the reactor, which was placed in an oven. The reaction temperature was measured by a thermocouple placed in the catalytic bed.

The gaseous effluents were analysed in-line by gas chromatography using a MicroGC equipped with three columns (molecular sieve, Plot U and OV-1).

A stream of helium and oxygen passed through the evaporator/saturator, which were adjusted to suitable temperatures that made it possible to obtain the desired ethanol/oxygen/helium composition. The catalyst was mixed with a quadruple amount of silicon carbide in the glass reactor.

Calibration of the MicroGC was carried out with reference gas mixtures, and the condensable products were calibrated using the evaporator/saturator.

Example 8

According to the Invention 150 mg of the MFM3-MS catalyst (supplied by MAPCO) were mixed with 600 mg of silicon carbide and were charged into the reactor.

The catalyst was activated at a temperature of 340° C. under a helium/oxygen mixture (48 Nml·min$^{-1}$/12 Nml·min$^{-1}$) for 12 hours. Next, the temperature was decreased to 200° C. and the data were recorded. After stabilization, the efficiency of the catalyst was tested. After acquisition of the data, the temperature of the catalyst was increased to the following temperature: 200° C. then 230° C. and 260° C., where the data were recorded.

The flow rates of oxygen and helium were respectively 4.6 and 41 Nml·min$^{-1}$ and the temperature of the saturator was adjusted to obtain a molar fraction of ethanol of 30%, ethanol/$O_2$/He=30/7/63. 500 ppm (vol) of $SO_2$ were added to the gas stream.

The results as regards the conversions and selectivities obtained during the catalytic oxidation of ethanol, expressed as follows: A=acetaldehyde; DEE=1,1-diethoxyethane; EE=ethyl ether; EA=ethyl acetate; AA=acetic acid; E=ethylene; CO=carbon monoxide; $CO_2$=carbon dioxide, are given in table 3.

TABLE 5

| Temperature (° C.) | Ethanol conversion (%) | Carbon selectivities (%) | | | | | | | |
|---|---|---|---|---|---|---|---|---|---|
| | | A | DEE | EE | EA | AA | E | CO | $CO_2$ |
| 201 | 5 | 52.0 | 45.0 | 3.0 | — | — | — | — | — |
| 231 | 10.8 | 61.7 | 34.3 | 4.0 | — | — | — | — | — |
| 260 | 25.6 | 70.0 | 23.6 | 6.2 | — | — | 0.2 | — | — |

Example 9

The preceding example was reproduced but without $SO_2$.

TABLE 6

| Temperature (° C.) | Ethanol conversion (%) | Carbon selectivities (%) | | | | | | | |
|---|---|---|---|---|---|---|---|---|---|
| | | A | DEE | EE | EA | AA | E | CO | $CO_2$ |
| 201 | 5 | 62 | 36 | 2 | — | — | — | — | — |
| 230 | 10.1 | 68.5 | 28.5 | 3 | — | — | — | — | — |
| 261 | 25.2 | 77.6 | 17.7 | 4.1 | — | — | 0.6 | — | — |

The invention claimed is:

1. A method for the synthesis of a dialkoxy alkane, as a primary reaction product, corresponding to the general formula: RR'CH—O—CRR'—O—CHRR' in which R and R' are either H, or a $CH_3$—$(CH_2)_n$— radical, n being between 0 and 2 and such that the total number of carbon atoms of the R and R' radicals is ≤3, said method consists of
   selectively oxidizing a part of an amount of a light alcohol comprising from 1 to 4 carbon atoms, in the presence of oxygen and a solid oxidation catalyst in a reaction medium comprising a gas phase containing an acid compound selected from the group consisting of $SO_3$, $SO_2$, and $NO_2$ having, in solution in water, a pKa of less than 6.3, wherein the amount of the acid compound is between 1 and 3000 ppm of the gaseous fraction of the reaction medium, to give an aldehyde, and
   reacting said aldehyde with the remainder of the amount of the light alcohol to give the dialkoxy alkane,
   wherein the solid oxidation catalyst is based on molybdenum in oxide form corresponding to the general formula:

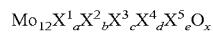

$$Mo_{12}X^1_a X^2_b X^3_c X^4_d X^5_e O_x$$

wherein Mo=molybdenum; O=oxygen; $X^1$=at least one element selected from the group consisting of iron, nickel, cobalt, manganese, tin, and copper; $X^2$=at least one element selected from the group consisting of bismuth, antimony, tellurium, indium, aluminum, and chromium; $X^3$=at least one element selected from the group consisting of phosphorus, tungsten, titanium, vanadium, tantalum, and niobium; $X^4$=at least one element selected from the group consisting of alkaline-earth metals, lanthanum, and cerium; $X^5$ is at least one element selected from the group consisting of alkali metals; and a, b, c, d and e are indices, the values of which are 0≤a≤20; 0≤b≤4; 0≤c≤5; 0≤d≤2; 0≤e≤2 such that a+b>0; and x is a numerical value determined by the degree of oxidation of the other elements, and optionally comprising silicon,
   wherein the oxidation reaction is carried out by contact in the vapor phase at a temperature between 100 and 350° C., under a pressure between 100 and 500 kPa with a space velocity for the introduction of the reaction mixture of between 2000 and 100 000 h$^{-1}$.

2. The method as claimed in claim 1, wherein the catalyst is selected from the group consisting of mixed oxides of formulae: $Mo_{12}BiFe_{3.7}Co_{4.7}Ni_{2.6}K_{0.09}Sb_1Si_{7.9}O_x$, $Mo_{12}BiFe_{3.7}Co_{4.7}Ni_{2.6}K_{0.09}Ti_{0.5}Si_{19}O_x$, and $MoO_3$—$Fe_2(MoO_4)_3$.

3. The method as claimed in claim 1, wherein the light alcohol is selected from the group consisting of methanol, ethanol, 1-propanol, isopropanol, n-butanol, and 2-butanol.

4. The method as claimed in claim 1, wherein said temperature is between 200° C. and 300° C.

5. The method as claimed in claim 1, wherein said space velocity for the introduction of the reaction mixture is between 11 000 and 44 000 h$^{-1}$.

6. The method as claimed in claim 1, wherein the catalyst is a mixed oxide based on molybdenum and iron.

7. The method as claimed in claim 1, wherein all the carbon atoms of the dialkoxy alkane originate from the amount of the light alcohol.

* * * * *